United States Patent
Chang et al.

(10) Patent No.: US 10,070,535 B2
(45) Date of Patent: Sep. 4, 2018

(54) WATERPROOF STRUCTURE FOR IMPLANTED ELECTRONIC DEVICE

(71) Applicant: GiMer Medical Co., Ltd., New Taipei (TW)

(72) Inventors: Chi-Heng Chang, New Taipei (TW); Chan-Yi Cheng, New Taipei (TW); Chen-Tun Wu, New Taipei (TW)

(73) Assignee: GIMER MEDICAL CO., LTD., New Taipei (TW)

( * ) Notice: Subject to any disclaimer, the term of this patent is extended or adjusted under 35 U.S.C. 154(b) by 0 days.

(21) Appl. No.: 15/788,328

(22) Filed: Oct. 19, 2017

(65) Prior Publication Data

US 2018/0042120 A1    Feb. 8, 2018

Related U.S. Application Data

(62) Division of application No. 15/343,759, filed on Nov. 4, 2016, now Pat. No. 9,848,497.

(30) Foreign Application Priority Data

Nov. 5, 2015  (CN) .......................... 2015 1 0744140

(51) Int. Cl.
| | |
|---|---|
| *H05K 1/00* | (2006.01) |
| *H05K 3/28* | (2006.01) |
| *A61N 1/375* | (2006.01) |
| *A61N 1/362* | (2006.01) |
| *A61N 1/36* | (2006.01) |

(Continued)

(52) U.S. Cl.
CPC ......... *H05K 3/285* (2013.01); *A61B 5/14503* (2013.01); *A61B 5/14532* (2013.01); *A61B 5/686* (2013.01); *A61N 1/362* (2013.01); *A61N 1/3605* (2013.01); *A61N 1/375* (2013.01); *H05K 1/0326* (2013.01); *H05K 3/0011* (2013.01); *A61B 2562/18* (2013.01); *H05K 2201/0162* (2013.01); *H05K 2201/0195* (2013.01); *H05K 2201/09063* (2013.01); *H05K 2203/1338* (2013.01); *H05K 2203/1377* (2013.01)

(58) Field of Classification Search
CPC .. H05K 1/02; H05K 1/09; H05K 3/28; H05K 3/38; A61N 1/372; A61N 1/375; H01L 23/02; H01L 23/10; H01L 23/52
USPC ......... 174/258, 250, 255–257; 361/302, 708, 361/728, 757, 816; 600/37, 561; 607/36
See application file for complete search history.

(56) References Cited

U.S. PATENT DOCUMENTS 4,424,147 A    1/1984  Kurz
4,774,434 A *  9/1988  Bennion ............. A41D 27/085
                                               257/E33.056

(Continued)

*Primary Examiner* — Xiaoliang Chen
(74) *Attorney, Agent, or Firm* — Muncy, Geissler, Olds & Lowe, P.C.

(57) ABSTRACT

A waterproof structure for an implanted electronic device is capable of preventing the liquid or moist from entering and damaging the circuit board of the electronic device. The waterproof structure includes a shell, a first material layer, a second material layer, and a third material layer. The first material layer covers at least a part of the implanted electronic device. The second material layer covers the first material layer. The internal space of the shell is configured for accommodating the implanted electronic device. The shell is made of PEEK (polyether ether ketone). The third material layer is disposed between the second material layer and the shell.

5 Claims, 4 Drawing Sheets

(51) Int. Cl.
*A61B 5/145* (2006.01)
*H05K 1/03* (2006.01)
*H05K 3/00* (2006.01)
*A61B 5/00* (2006.01)

(56) References Cited

U.S. PATENT DOCUMENTS

| | | | |
|---|---|---|---|
| 5,130,600 A * | 7/1992 | Tomita | G01P 1/006 |
| | | | 310/319 |
| 5,358,878 A | 10/1994 | Suchet | |
| 5,532,613 A | 7/1996 | Nagasawa | |
| 5,867,371 A * | 2/1999 | Denzene | H05K 3/284 |
| | | | 174/386 |
| 6,204,454 B1 | 3/2001 | Gotoh | |
| 6,498,951 B1 | 12/2002 | Larson | |
| 9,254,588 B1 * | 2/2016 | Chao | H05K 3/284 |
| 9,318,135 B2 | 4/2016 | Nojima | |
| 2002/0102047 A1 | 8/2002 | Akkaraju | |
| 2002/0173199 A1 * | 11/2002 | Liegl | H01R 13/5216 |
| | | | 439/519 |
| 2004/0201947 A1 | 10/2004 | Stevenson | |
| 2004/0219184 A1 | 11/2004 | Brown | |
| 2005/0263482 A1 | 12/2005 | Takakusaki | |
| 2005/0277960 A1 | 12/2005 | Hassler, Jr. | |
| 2006/0018098 A1 | 1/2006 | Hill | |
| 2006/0161186 A1 | 7/2006 | Hassler, Jr. | |
| 2006/0247664 A1 | 11/2006 | Meng | |
| 2006/0259015 A1 | 11/2006 | Steinbach | |
| 2007/0080415 A1 | 4/2007 | Cho | |
| 2007/0112328 A1 | 5/2007 | Steinbach | |
| 2008/0035369 A1 | 2/2008 | Joodaki | |
| 2008/0089179 A1 | 4/2008 | Matsumoto | |
| 2008/0139959 A1 * | 6/2008 | Miethke | A61B 5/0031 |
| | | | 600/561 |
| 2009/0148496 A1 | 6/2009 | Schmitz | |
| 2009/0299216 A1 | 12/2009 | Chen | |
| 2010/0041091 A1 | 2/2010 | Axelrod | |
| 2010/0133677 A1 | 6/2010 | Murayama | |
| 2010/0157545 A1 | 6/2010 | Lehtimaki | |
| 2010/0164083 A1 | 7/2010 | Yim | |
| 2010/0193927 A1 * | 8/2010 | Nishikawa | G06K 19/077 |
| | | | 257/679 |
| 2011/0029087 A1 | 2/2011 | Haider | |
| 2011/0058831 A1 | 3/2011 | Usami | |
| 2011/0063176 A1 | 3/2011 | Byrum | |
| 2011/0112608 A1 | 5/2011 | Zierhofer | |
| 2011/0270028 A1 * | 11/2011 | Honaryar | A61F 5/0013 |
| | | | 600/37 |
| 2012/0006789 A1 | 1/2012 | DeNatale | |
| 2012/0176703 A1 | 7/2012 | Nojima | |
| 2012/0237250 A1 | 9/2012 | Higa | |
| 2012/0253270 A1 | 10/2012 | Steinbach | |
| 2013/0015570 A1 | 1/2013 | Sato | |
| 2013/0317288 A1 * | 11/2013 | Honaryar | A61F 5/0013 |
| | | | 600/37 |
| 2013/0341516 A1 | 12/2013 | Ishida | |
| 2014/0001366 A1 | 1/2014 | Nishida | |
| 2014/0001367 A1 | 1/2014 | Anzai | |
| 2014/0063822 A1 | 3/2014 | Sasaki | |
| 2014/0120413 A1 | 5/2014 | Nielsen | |
| 2015/0140512 A1 | 5/2015 | Bachler | |
| 2015/0247934 A1 | 9/2015 | Toyama | |
| 2015/0251397 A1 | 9/2015 | Lee | |
| 2015/0257253 A1 | 9/2015 | Lee | |
| 2016/0100887 A1 | 4/2016 | Wu | |

* cited by examiner

WATERPROOF STRUCTURE FOR IMPLANTED ELECTRONIC DEVICE

CROSS REFERENCE TO RELATED APPLICATIONS

This application is a Divisional of co-pending application Ser. No. 15/343,759 filed on Nov. 4, 2016, which claims priority under 35 U.S.C. § 119(a) on Patent Application No(s). 201510744140.4 filed in People's Republic of China on Nov. 5, 2015, and the entire contents of which are herein incorporated by reference in its entirety.

BACKGROUND OF THE INVENTION

Field of Invention

The present invention relates to a waterproof structure for an implanted electronic device, and in particular, to a waterproof structure with multiple layers.

Related Art

Today, the precise micro-processes have be developed. In some researches, the electronic devices can be miniaturized and implanted into the organisms. Such implantations of electronic devices are commonly used for treatment or detection purposes. In order to ensure the safety and life of implanted medical electronic devices, it is important to provide a proper prevention mechanism of liquid infiltration.

In order to achieve the waterproof and moisture-proof functions for electronic devices, the components of the electronic device, such as connectors or shell holes, must be tightly bonded to prevent or delay the water and moist from entering the electronic device through the shell holes, which may result in problems such as oxidation of the electronic components. In addition, the infiltration of moisture may cause damage to the circuit board of the electronic device, and the damaged electronic device may further harm the human body. Accordingly, the implanted medical electronic devices must have a more stringent waterproof structure to avoid the danger of patients.

In general, the shell with waterproof function is used for achieving the purposes of waterproof and moisture-proof. For example, US Patent Application No. 2011/0112608A1 discloses a special waterproof shell for preventing the body liquid or moisture from entering the electronic device. In addition, the conventional art also discloses an approach to provide a rubber element on the gaps of the shell of the electronic device for sealing the connection between the connector and the device body, thereby preventing the moisture from entering the electronic device. However, the implanted medical electronic devices have higher risk to be damaged by the moisture than the general electronic devices. Accordingly, only a single shell structure is not good enough for the complete waterproof approach, and an advanced protection mechanism is needed for the implanted medical electronic devices so as to prevent the danger of the patients.

Therefore, it is desired to provide a waterproof structure for an implanted medical electronic device, which can perfectly block the body liquid and moisture and provide a safety protection once the electronic device is damaged.

SUMMARY OF THE INVENTION

In view of the foregoing, an objective of the present invention is to provide a waterproof structure for an implanted medical electronic device, which can prevent the body fluid or moisture from entering the electronic device and damaging the circuit board.

To achieve the above objective, the present invention discloses a waterproof structure applied to a circuit board of an implanted medical electronic device. The waterproof structure includes a shell, a first material layer, a second material layer, and a third material layer. The first material layer covers at least a part of the implanted electronic device. The second material layer covers the first material layer. The shell has an internal space for accommodating the implanted electronic device, and the shell is made of PEEK (polyether ether ketone). The third material layer is disposed between the second material layer and the shell.

In one embodiment, the third material layer is disposed between the second material layer and the shell, so that a porosity in the shell is less than 5%.

In one embodiment, each of the first material layer and the third material layer is made of epoxy or silicone.

In one embodiment, the second material layer includes poly-para-xylene or a combination of aluminum oxide and titanium oxide.

In one embodiment, the shell has at least two through holes.

In addition, the present invention also discloses a manufacturing method of a waterproof structure applied to a circuit board of an implanted electronic device. The manufacturing method includes the following steps of: forming a first material layer on the circuit board for covering at least a part of the circuit board; forming a second material layer for covering the first material layer; after forming the second material layer, disposing the circuit board, the first material layer and the second material layer in a shell, wherein the shell is made of PEEK (polyether ether ketone); and filling a third material layer between the second material layer and the shell.

In one embodiment, the second material layer includes poly-para-xylene, and the second material layer is formed by CVD (chemical vapor deposition).

In one embodiment, the second material layer includes a combination of aluminum oxide and titanium oxide, and the second material layer is formed by ALD (atomic layer deposition).

The present invention utilizes a waterproof structure with three layers for improving the protection of the electronic device, so that the body fluid or moisture can be blocked. Even the body fluid or moisture penetrates through the shell, the waterproof structure can still protect the implanted electronic device from the body fluid or moisture.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

To be noted, the implanted electronic device is a medical electronic device that can be implanted into the animal body. For example, the medical electronic device can be an implantable nerve stimulator, a blood glucose sensor, or an artificial pacemaker. The animal body is a mammal such as mouse, human, rabbit, cow, sheep, pig, monkey, dog, cat and the like, and is preferably human. Besides, the waterproof structure of the implanted electronic device of this invention is not limited to the medical electronic device. However, in the following embodiments, the implanted electronic device is an implantable nerve stimulator for spine, which can heal or release the pain of human body.

Figure 1:
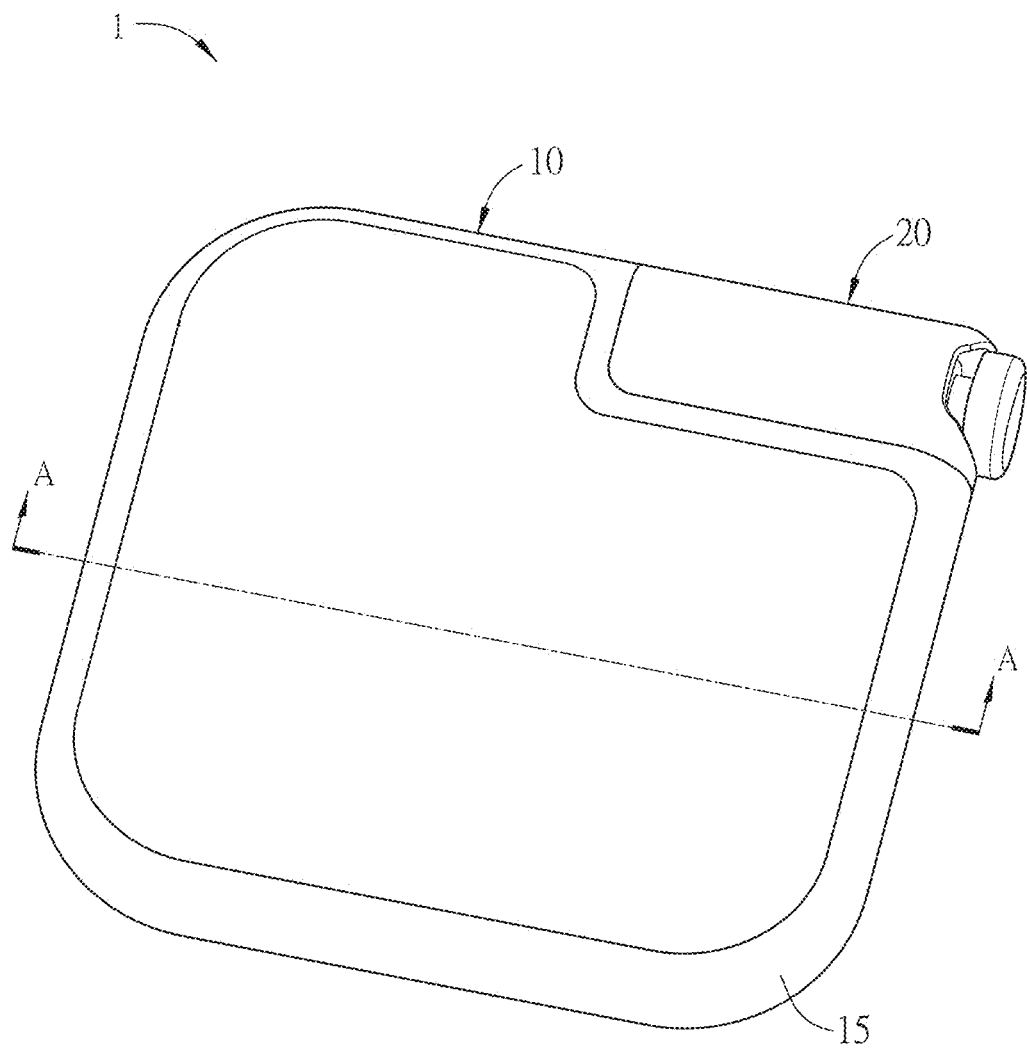
FIG. 1 is a schematic diagram showing a waterproof structure of an implanted electronic device.
Figure 2:
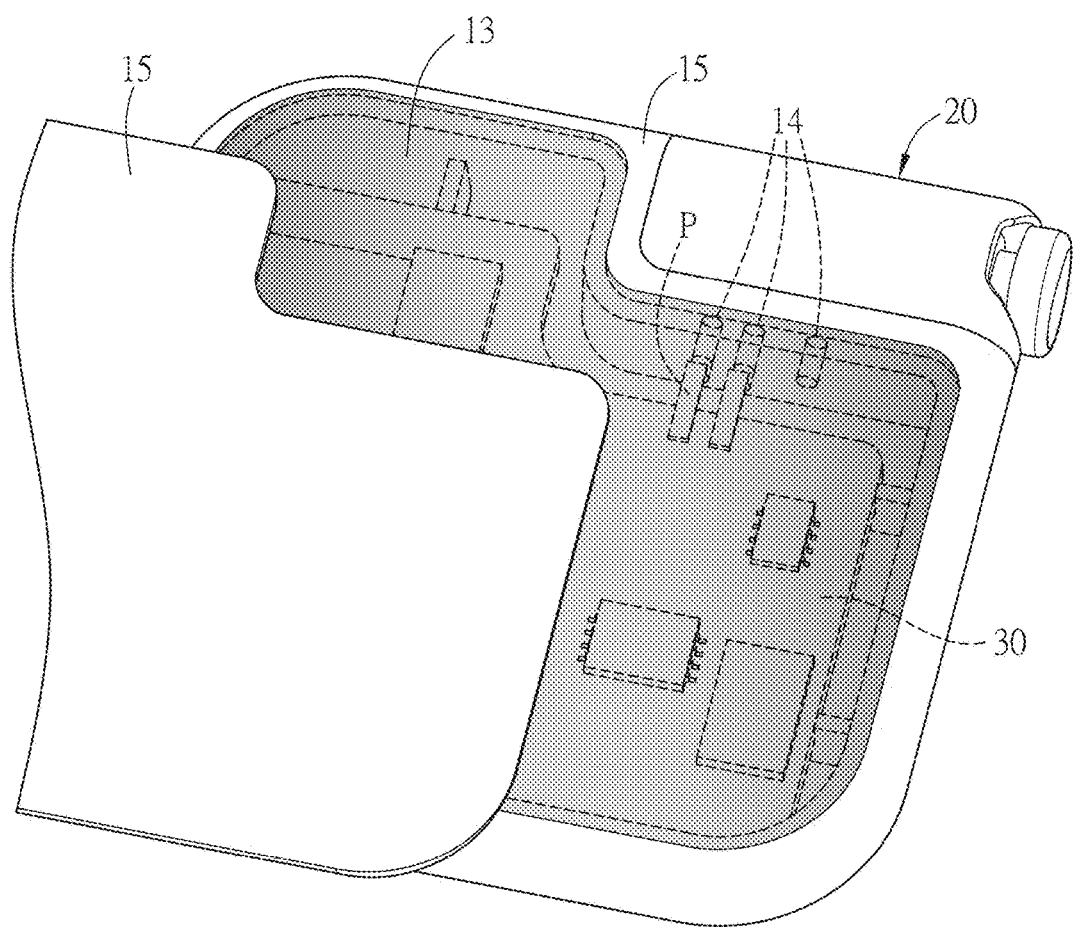
FIG. 2 is a schematic diagram showing the internal structure of the implanted electronic device.

FIG. 1 is a schematic diagram showing a waterproof structure of an implanted electronic device, and FIG. 2 is a schematic diagram showing the internal structure of the implanted electronic device. Referring to FIGS. 1 and 2, the implanted electronic device 1 includes a waterproof structure 10, a connector 20 and a circuit board 30. The waterproof structure 10 includes a shell 15, a first material layer 11, a second material layer 12, and a third material layer 13. The shell 15 accommodates the circuit board 30 of the implanted electronic device 1. The connector 20 is configured for coupling the circuit board 30 of the implanted electronic device 1 to an external control device for controlling the parameters of the implanted electronic device 1.

As shown in FIG. 2, the circuit board 30 of the implanted electronic device 1 must be electrically connected to the external control device for adjusting or setting the parameters. Thus, the shell 15 is configured with two or more through holes 14 for inserting the pins of the connector 20. In this embodiment, the shell 15 has three through holes 14, and the connector 20 has two pins inserting into the through holes 14 to contact with the conductive sheets P. The circuit board 30 of the implanted electronic device 1 is electrically connected to the two conductive sheets P. Accordingly, the circuit board 30 of the implanted electronic device 1 can be coupled to the external control device via the connector 20.

Figure 3A:
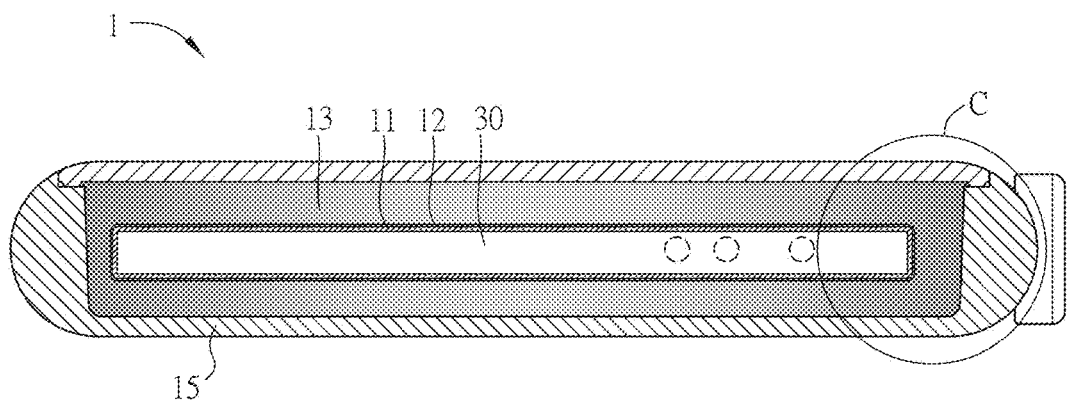
FIG. 3A is a sectional view of the waterproof structure of an implanted electronic device along the line A-A.
Figure 3B:
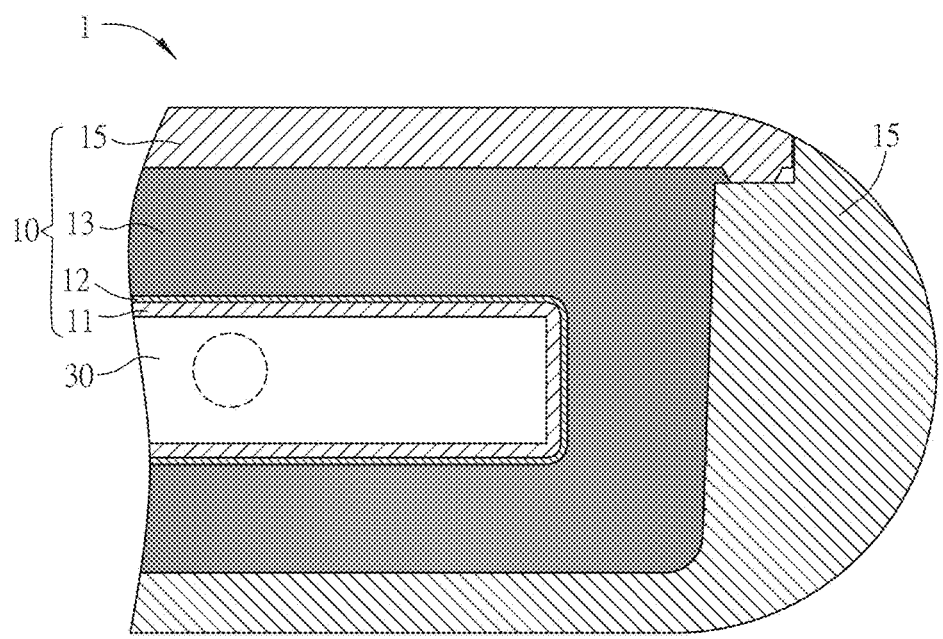
FIG. 3B is an enlarged view of the circle area C of FIG. 3A.

FIG. 3A is a sectional view of the waterproof structure of FIG. 1 along the line A-A, and FIG. 3B is an enlarged view of the circle area C of FIG. 3A. Referring to FIGS. 3A and 3B, the first material layer 11 covers almost the entire circuit board 30 of the electronic device 1 by molding, and only the contact points (not shown) of the conductive sheets P are not covered. The second material layer 12 is a very thin layer, so it will easily have a break over a non-planar surface, such as the electronic component of the circuit board 30 or the protrusion of the welding point. In this embodiment, the first material layer 11 can not only provide a waterproof and insulation function, but also reduce the protrusions on the circuit board 30. In other words, the first material layer 11 can provide a smooth surface to facilitate the deposition of the second material layer 12, thereby decreasing the risk of breaking the second material layer 12. Besides, the first material layer 11 can be formed on the circuit board 30 of the electronic device 1 (excepting the contact points) by coating, dispensing or immersion, and this invention is not limited.

The second material layer 12 can be formed by CVD (chemical vapor deposition) or ALD (atomic layer deposition). In more detailed, poly-para-xylene is stacked on the surface of the first material layer 11 by the CVD process so as to form the second material layer 12. Otherwise, a combination of aluminum oxide and titanium oxide is deposited on the surface of the first material layer 11 by the ALD process so as to form the second material layer 12. Of course, the second material layer 12 can also be formed by other materials having a molecular structure with tight arrangement, and this invention is not limited.

The third material layer 13 is made of epoxy or silicone. In practice, the epoxy or silicone is injected to the gap between the second material layer 12 and the shell 15 through the through holes 14 until the porosity in the shell 15 is less than 5%. In other words, the third material layer 13 can not only provide the waterproof and insulation function, but also fix the circuit board 30 of the electronic device 1, the first material layer 11 and the second material layer 12 in the shell 15. This configuration can protect the second material layer 12 from being broken by collision. In addition, the conductive sheets P for coupling the circuit board 30 are not covered by the first material layer 11 and the second material layer 12, and they protrude over the first material layer 11 and the second material layer 12 for connecting with the pins, which pass through the through holes 14. Accordingly, the fixing function of the third material layer 13 can further ensure the fixing of the welding point between the conductive sheet P and the pin, thereby preventing the detachment between the conductive sheet P and the pin.

In this embodiment, the shell is made of PEEK (polyether ether ketone), which has resistances for high temperature, corrosion and hydrolysis. Since the shell 15 of the electronic device 1 directly contacts with the human body, the biocompatible material (PEEK) can fabricate the shell with less harmful to human body. The first material layer 11 and the third material layer 13 can be made of epoxy or silicone, which has the properties of high temperature resistance, waterproof and insulation. Accordingly, using these materials (epoxy or silicone) to cover the circuit board 30 of the electronic device 1 can prevent the leakage of moisture or body fluid so as to protect the inside circuit board 30. Moreover, when the circuit board 30 has short circuit, this configuration can also protect the human body from the possible electric shock or burn. The second material layer 12 can be made of poly-para-xylene or a combination of aluminum oxide and titanium oxide. Since the material of the second material layer 12 has a molecular structure with tight arrangement, the external water molecules can be perfectly blocked so as to achieve the purpose of blocking water and moisture.

Figure 4:
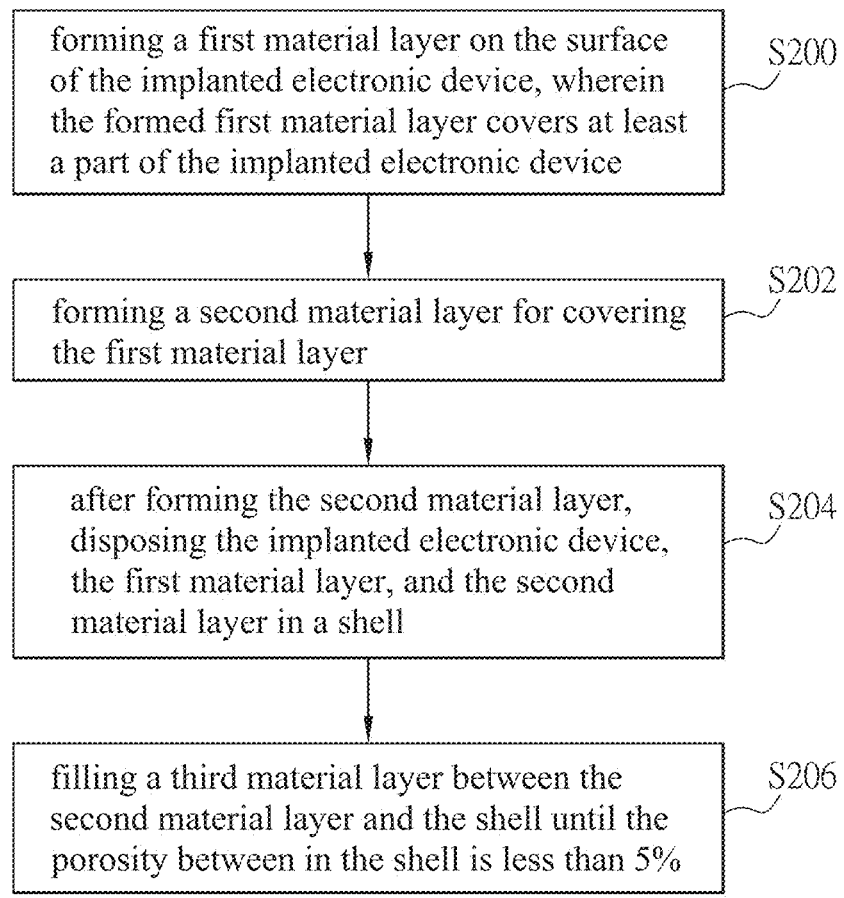
FIG. 4 is a flow chart of a manufacturing method of the waterproof structure of FIG. 1.

FIG. 4 is a flow chart of a manufacturing method of the waterproof structure of FIG. 1. To be noted, the steps of the manufacturing method of the waterproof structure can be switched only if the desired result can be obtained. The manufacturing method of the waterproof structure of FIG. 1 generally includes the following steps:

Step 200: forming a first material layer 11 on the surface of the implanted electronic device 1, wherein the formed first material layer 11 covers at least a part of the implanted electronic device 1.

Step 202: forming a second material layer 12 for covering the first material layer 11.

Step 204: after forming the second material layer 12, disposing the implanted electronic device 1, the first material layer 11, and the second material layer 12 in a shell 15.

Step 206: filling a third material layer 13 between the second material layer 12 and the shell 15 until the porosity between in the shell 15 is less than 5%.

Those skilled persons in the art can realize the steps described in FIG. 4 after viewing the above embodiments, so the detailed description thereof will be omitted.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A manufacturing method of a waterproof structure applied to a circuit board of an implanted electronic device, comprising steps of:
    forming a first material layer on the circuit board for covering at least a part of the circuit board;
    forming a second material layer for covering the first material layer;
    after forming the second material layer, disposing the circuit board, the first material layer and the second material layer in a shell, wherein the shell is made of PEEK (polyether ether ketone); and
    filling a third material layer between the second material layer and the shell.

2. The manufacturing method of claim 1, wherein after filling the third material layer between the second material layer and the shell, a porosity in the shell is less than 5%.

3. The manufacturing method of claim 1, wherein each of the first material layer and the third material layer is made of epoxy or silicone.

4. The manufacturing method of claim 1, wherein the second material layer comprises poly-para-xylene, and the second material layer is formed by CVD (chemical vapor deposition).

5. The manufacturing method of claim 1, wherein the second material layer comprises a combination of aluminum oxide and titanium oxide, and the second material layer is formed by ALD (atomic layer deposition).

* * * * *